US010531974B2

(12) United States Patent
Hunter, Jr.

(10) Patent No.: US 10,531,974 B2
(45) Date of Patent: Jan. 14, 2020

(54) WRIST TOWER

(71) Applicant: Hunter Medical, LLC, Columbia, TN (US)

(72) Inventor: Alton Lee Hunter, Jr., Columbia, TN (US)

(73) Assignee: Hunter Medical, LLC, Columbia, TN (US)

( * ) Notice: Subject to any disclaimer, the term of this patent is extended or adjusted under 35 U.S.C. 154(b) by 354 days.

(21) Appl. No.: 15/381,828

(22) Filed: Dec. 16, 2016

(65) Prior Publication Data

US 2018/0168842 A1 Jun. 21, 2018

(51) Int. Cl.
*A61F 5/04* (2006.01)
*A61G 13/12* (2006.01)
*A61G 13/10* (2006.01)
*A61F 5/37* (2006.01)
*A61F 5/01* (2006.01)
*A61F 5/042* (2006.01)

(52) U.S. Cl.
CPC .............. *A61F 5/04* (2013.01); *A61F 5/0118* (2013.01); *A61F 5/042* (2013.01); *A61F 5/3761* (2013.01); *A61G 13/101* (2013.01); *A61G 13/124* (2013.01); *A61G 13/1235* (2013.01)

(58) Field of Classification Search
CPC .......... A61F 5/04; A61F 5/042; A61F 5/3761; A61F 5/3769; A61F 5/3792; A61G 13/101; A61G 13/1235; A61G 13/124; A61G 13/125
See application file for complete search history.

(56) References Cited

U.S. PATENT DOCUMENTS

| 473,200 A | 4/1892 | Streeter |
| 1,516,795 A | 11/1924 | Schwarting |
| 1,887,022 A | 11/1932 | Hoffman et al. |
| 4,220,146 A * | 9/1980 | Cloutier ............. A61B 17/6425 606/59 |
| 4,454,870 A * | 6/1984 | Schwentker .......... A61F 5/3707 128/869 |

(Continued)

FOREIGN PATENT DOCUMENTS

FR 2578417 A1 9/1986

OTHER PUBLICATIONS

U.S. Appl. No. 14/268,989, filed May 2, 2014, Hunter.

(Continued)

*Primary Examiner* — Kari K Rodriquez
(74) *Attorney, Agent, or Firm* — Waller Lansden Dortch & Davis, LLP; Matthew C. Cox

(57) ABSTRACT

A wrist tower attachment for an arm stabilizer device is configured for modular attachment on a support arm secured in a rail clamp mounted on a rail of an operating table. The wrist tower attachment includes a wrist tower base and a wrist tower post protruding upwardly from the wrist tower base. The support arm includes a stabilizer bar having a distal bar end, and the wrist tower attachment is secured onto the distal bar end. In some embodiments, the wrist tower attachment includes a female axial socket shaped to receive the male distal bar end. A traction bar is positioned on the wrist tower post and protrudes radially from the wrist tower post. A tension gauge is disposed on the traction bar in some embodiments.

7 Claims, 13 Drawing Sheets

(56) References Cited

U.S. PATENT DOCUMENTS

| | | | |
|---|---|---|---|
| 5,063,918 A * | 11/1991 | Guhl | A61B 17/6425 602/40 |
| 5,462,247 A | 10/1995 | Aldrich | |
| 5,537,702 A | 7/1996 | Brown-Milants et al. | |
| 5,785,057 A | 7/1998 | Fischer | |
| 5,884,974 A | 3/1999 | Bergsten et al. | |
| 5,904,655 A | 5/1999 | Brackett | |
| 5,961,512 A | 10/1999 | Purnell | |
| 6,467,487 B1 | 10/2002 | Rios | |
| 6,533,744 B1 | 3/2003 | Stanish et al. | |
| 6,629,944 B2 | 10/2003 | Smart | |
| 6,758,827 B2 | 7/2004 | Moss | |
| 7,017,215 B1 | 3/2006 | Singer et al. | |
| 7,143,458 B2 | 12/2006 | Slater, Jr. | |
| 7,441,293 B1 | 10/2008 | Singer et al. | |
| 7,634,828 B2 | 12/2009 | Elhabashy | |
| 7,686,775 B2 | 3/2010 | Branch | |
| 7,771,378 B2 | 8/2010 | Price et al. | |
| 7,832,035 B2 | 11/2010 | Walczyk | |
| 8,230,864 B2 | 7/2012 | Hunter | |
| 8,273,043 B2 | 9/2012 | Bonutti et al. | |
| 8,286,283 B2 | 10/2012 | Copeland et al. | |
| 8,356,601 B2 | 1/2013 | Hunter | |
| 8,545,373 B2 | 10/2013 | Borden | |
| 9,271,862 B2 | 1/2016 | Hunter | |

OTHER PUBLICATIONS

Schure Med, 2016 Patient Positioning Catalog, 37 pages, dated Jan. 2016.
Allen Medical, Orthopaedics Catalog, 31 pages, dated Sep. 2016.
Acumed, Arc Wrist Tower, 12 pages, dated Jan. 2009.
Smith & Nephew, Tenet Medical Engineering, Tenet Wrist Tower, 4 pages, dated Sep. 2009.

\* cited by examiner

WRIST TOWER

BACKGROUND

The present invention relates generally to orthopedic positioning devices and more particularly to devices and methods for supporting an arm, wrist and hand before, during or after a surgical, rehabilitative or imaging procedure.

Surgical procedures on the extremities of humans occur with great frequency, and particularly surgeries on the arm, wrist and hand. Injuries to a person's arm, wrist and hand come frequently from sports injuries, falls, reaching to catch one's self, slipping or landing on an arm, wrist or hand, and attempting to brace oneself in response to a fall resulting in fractured bones in the forearm, wrist and/or hand.

During the course of some procedures to repair injury to the arm, wrist and/or hand, a patient's arm may be placed in a supine suspended orientation to reduce a fracture or distract the hand, wrist or forearm. Additionally, this position may provide a desired orientation of the hand, wrist or forearm for a procedure. In this position, a patient's fingers or wrist may be suspended vertically by an overhead support structure including one or more straps, finger traps or anchors extending downwardly and engaging the patient. In this configuration, a patient's arm, wrist or hand may be subjected to vertical traction forces to provide proper positioning for a surgical procedure or rehabilitation.

Others have attempted to provide devices for supporting a patient's arm, wrist and/or hand in a supine suspended position for a surgical or rehabilitative procedure. Conventional devices commonly include an upright pole from which one or more traction attachments for supporting the arm, wrist or hand are suspended. For example, U.S. Pat. No. 7,771,378 teaches an orthopedic traction tower system.

Conventional devices of this type are configured only for application of distraction forces on a hand or wrist and lack interchangeability with other modular support components for positioning of the arm, wrist and hand in different orientations for other operations. Additionally, conventional support devices are not configured to receive modular attachments for applying counter-traction forces. This leads to a requirement that a surgeon must have numerous independent positioner devices for performing different types of procedures on the hand, wrist, forearm and elbow. This leads to additional cost and clutter associated with numerous positioner devices for different patient orientations and procedures. Thus, there is a continuing need in the art for improvements in devices and methods for supporting an arm for such purposes, and particularly to universal positioner devices for allowing physicians to interchange modular attachments to achieve various patient orientations with a single system.

What is needed, then are improvements in devices and methods for supporting and distracting a patient's arm, hand, elbow and/or wrist during a surgical or rehabilitative procedure.

BRIEF SUMMARY

The present invention generally provides devices and associated methods for stabilizing a hand and/or arm during a surgical or rehabilitative procedure, during resting, during medical imaging of the hand and/or arm, or during other times when it is desirable to have a hand and/or arm stabilized in a stationary position.

In some embodiments, the present invention provides a rail clamp for attachment to a rail or other structure on a patient table such as an operating or surgical table. One or more attachments can be detachably secured to the rail clamp to provide distraction of a patient's arm, wrist and/or hand. Each attachment is also included as a part of the invention.

In further embodiments, the present invention provides a wrist distraction tower securable to a rail clamp on an operating table. The wrist distraction tower includes an arm support having a stabilizer bar and a base in some embodiments. The base is configured to secure to the rail clamp such that the stabilizer bar extends upwardly away from the rail clamp. The base includes a rod that slides vertically into a corresponding socket in the rail clamp in some embodiments.

A wrist tower attachment is provided for attachment to the stabilizer bar in in some embodiments. The wrist tower attachment includes a tower base disposed on the distal end of the stabilizer bar and a tower post extending upwardly from the tower base. The tower post may include a threaded region in some embodiments. A moveable tower hanger is disposed on the tower post. The tower hanger may be positioned at various locations along the length of the tower post in various embodiments. One or more traction straps may be suspended from the traction hanger and engage a portion of a user's arm, wrist or hand. In some embodiments, a traction gauge is disposed between the traction hanger and the traction straps allowing a provider to monitory the tensile traction forces applied to the user's arm, wrist and/or hand by the wrist tower apparatus.

A humeral support attachment may also be detachably secured to the rail clamp to further support a patient's humeral region during use of the wrist tower apparatus. The humeral support attachment includes a humeral support mount that engages and secures to the rail clamp and a humeral support bar extending from the humeral support mount in a direction away from the rail clamp. The humeral support bar provides support to a user's humeral region during use. One or more humeral support pads may be positioned on the humeral support bar to pad a patient's arm during use.

A reducer attachment is also detachably secured to the stabilizer bar in some embodiments. The reducer attachment includes a reducer mount that engages and secures to the stabilizer bar in some embodiments. A reducer attachment bar extends from the reducer attachment mount generally away from the stabilizer bar to provide a support for a patient's arm during use.

In some embodiments, the present disclosure provides an arm positioner system having multiple modular attachments for positioning a patient's arm, elbow, wrist and/or hand in a desired position for various surgical, rehabilitative or imaging procedures. The system includes a rail clamp, a removable arm support having a stabilizer bar and a base received in the rail clamp, a modular wrist support attachment detachably securable to the stabilizer bar, a reducer attachment detachably securable to the stabilizer bar, a humeral support detachably securable to the rail clamp or stabilizer bar, and a wrist distraction tower attachment detachably securable to the stabilizer bar.

When the system is used for wrist distraction in a suspended supine position, the apparatus is positioned with the stabilizer bar oriented upwardly from the rail clamp, and the wrist distraction tower is installed on the distal end of the support bar.

Alternatively, when the system is used for elbow surgery such as supine or lateral decubitus procedures, elbow arthroscopy, elbow arthroplasty, ulnar nerve surgery, olecranon bursa excisions or other operations, the system may be configured for an operation using the rail clamp, the stabilizer bar installed on the rail clamp, the humeral support attachment installed on the rail clamp, the reducer attachment installed on the stabilizer bar, and the wrist support disposed on the distal end of the stabilizer bar.

In further embodiments, the system includes a lateral positioner device including a rail clamp and a lateral positioner device installed on the rail clamp. The lateral positioner device includes a lateral support post configured to engage the rail clamp. A lateral brace is disposed on the lateral support post. In some embodiments, the lateral support post slides into a corresponding socket on the rail clamp to secure the post to the rail clamp.

The support device of the present disclosure provides a single system with numerous modular attachments that may be use individually or in combination to achieve desired positioning of a patient's arm, wrist or hand.

Numerous other objects, features and advantages of the present invention will be readily apparent to those skilled in the art upon a reading of the following disclosure when taken in conjunction with the accompanying drawings.

DETAILED DESCRIPTION

Figure 1:
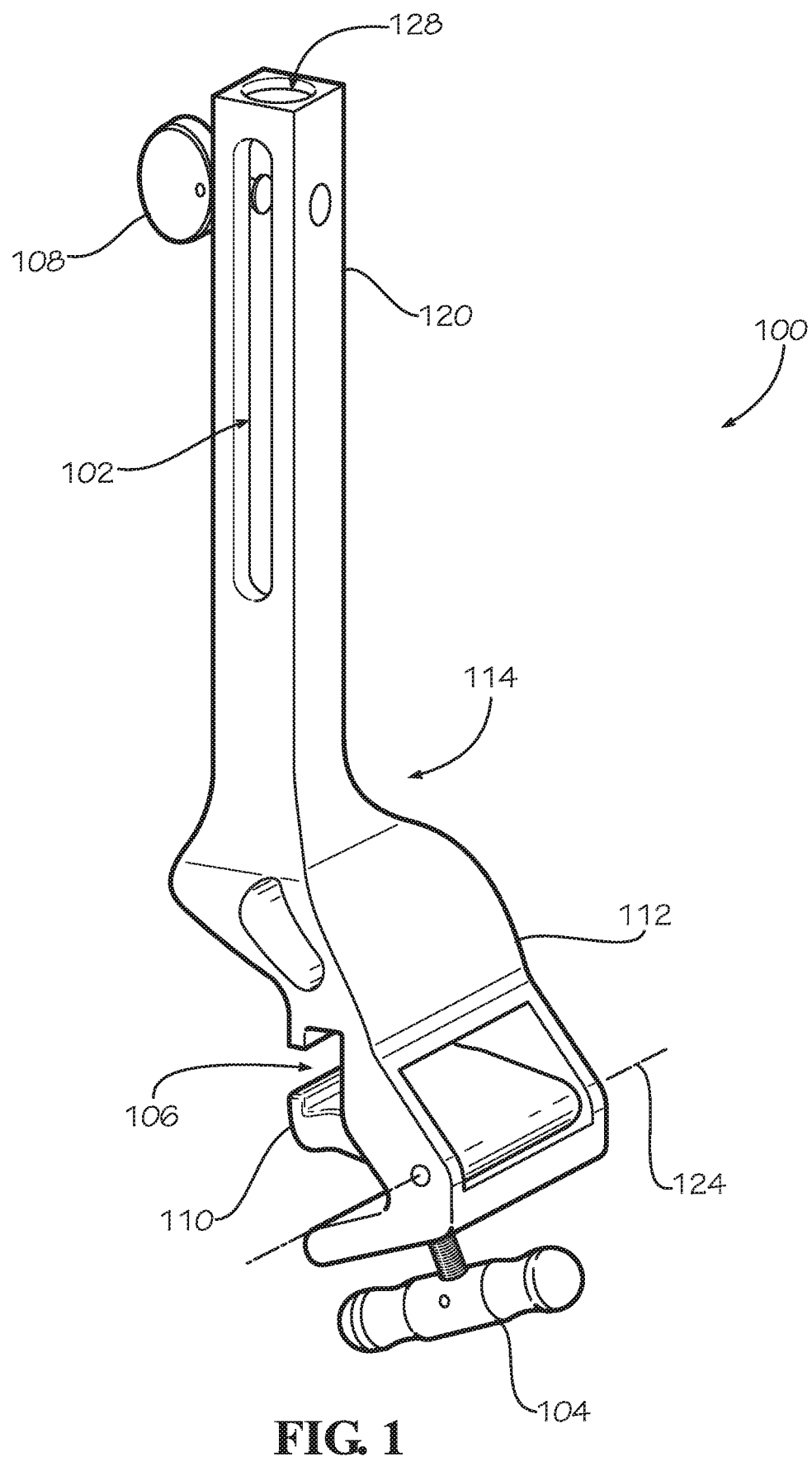
FIG. 1 illustrates a perspective view of an embodiment of a rail clamp in accordance with the present disclosure.

Referring now to the drawings, various views of embodiments of an arm positioner, or arm stabilizer device, and components therefor are illustrated. In the drawings, not all reference numbers are included in each drawing, for the sake of clarity. In addition, positional terms such as "upper," "lower," "side," "top," "bottom," "vertical," "horizontal" etc. refer to the apparatus when in the orientation shown in the drawings or similar orientations. A person of skill in the art will recognize that the apparatus can assume different orientations when in use.

An arm positioner device is typically used for securing a patient's arm, wrist or hand during a medical procedure, such as during a surgery, during imaging, or during a rehabilitative operation. Generally, when a patient is lying in a supine position, it is desirable in some applications to place the patient's arm in a suspended supine orientation where the patient's hand and fingers extend upwardly above the elbow joint. The present disclosure provides an arm stabilizer apparatus including a wrist tower attachment. The wrist tower attachment is a modular component that can included as part of a modular arm positioner system. The wrist tower attachment may be assembled onto the arm positioner device when it is desirable to place a patient's arm, wrist or hand in a supine suspended orientation for fracture reduction or distraction of the forearm, wrist or hand. The apparatus may be disassembled for storage, sterilization or transport. Other modular attachments may be installed onto the modular positioning system to provide other patient orientations. By providing an apparatus that may be disassembled into component attachments, the overall form factor of the device may be reduced when the individual components are disassembled.

Referring further to the drawings, FIG. 1 illustrates an embodiment of a rail clamp 100, or base support, in accordance with the present disclosure. Rail clamp 100 is generally configured for attachment to a side rail or other similar structure on a table such as an operating table or a surgical table. Similar types of rails may be found on other structures for supporting or transporting patients. Rails of this nature include a universal mounting configuration in some applications to allow for interchangeability of attachments. Rail clamp 100 includes a clamp base 112 having a clamp jaw 110, or pawl, that is hinged about a pawl axis 124 on the clamp base 112. A mounting recess 106 is defined between clamp base 112 and clamp jaw 106 shaped to receive the rail on which rail clamp 100 is to be mounted. A rail clamp fastener 104 allows clamp jaw 110 to be tightened against the rail. A handle is positioned on the rail clamp fastener 104 to allow for manual adjustment of the force applied to clamp jaw 110.

Figure 2:
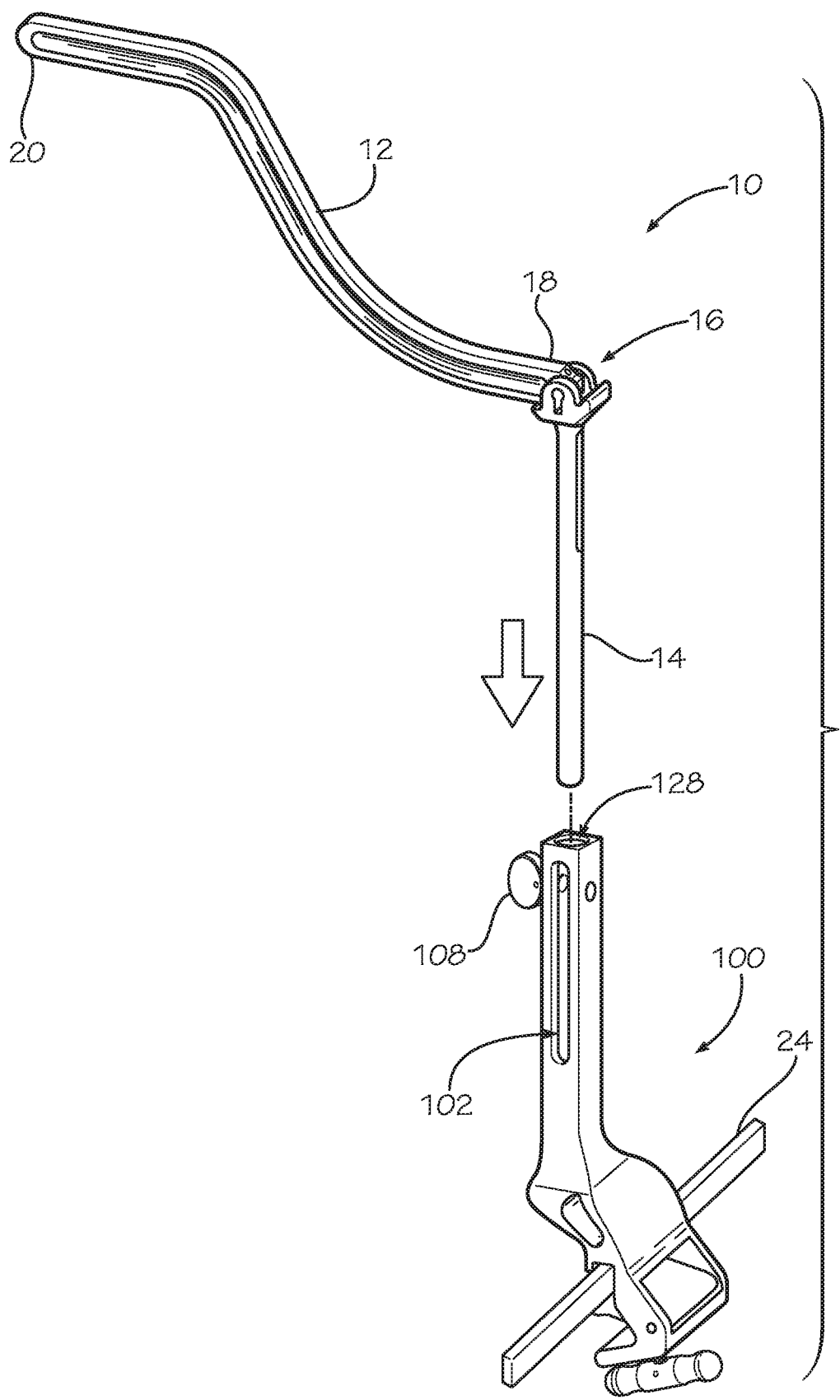
FIG. 2 illustrates a partially exploded perspective view of an embodiment of a rail clamp and arm support in accordance with the present disclosure.

Rail clamp 100 may be positioned along the longitudinal length of a rail 24, shown in FIG. 2, by simply loosening the rail clamp fastener 104, repositioning the rail clamp 100, and then re-tightening the rail clamp fastener 104. This allows the rail clamp 100 to be moved relative to a patient's location on the table.

Rail clamp 100 is a modular support base for an arm positioner system. Rail clamp 100 is further configured to receive multiple modular attachments for use in supporting a patient's arm or other extremity during use. Rail clamp 100 includes a mounting body 120, or clamp body, protruding upwardly from the clamp base 112. Mounting body 120 includes a longitudinal section that is configured to extend generally upwardly away from the rail during use. A longitudinal socket 128 is defined in the rail clamp 100 in some embodiments. Socket 128 is shaped to receive a portion of a separate modular component of the arm positioner system in the socket.

As seen in FIG. 2, one type of modular attachment for installation on rail clamp 100 includes an arm support 10, or supine positioner. Arm support 10 includes a stabilizer bar 12 and a base 14. The stabilizer bar 12 is pivotally attached to the base 14 in some embodiments. In alternative embodiments, stabilizer bar 12 and base 14 include a rigid configuration on arm support 10. Base 14 includes a longitudinal shaft in some embodiments. The shaft on base 14 is shaped to be inserted longitudinally in socket 128 on rail clamp 100 in some embodiments. The shaft may form a rod having a round, oval or polygonal cross-sectional profile in various embodiments. The shaft of base 14 is dimensioned to fit in socket 128 on rail clamp 100. The shaft may be loaded into socket 128 in a generally vertical orientation after rail clamp 100 is secured to a rail on a table. Alternatively, the shaft of base 14 may be installed into the socket 128 on rail clamp 100 prior to attachment of rail clamp 100 to the rail on the operating table.

Figure 3:
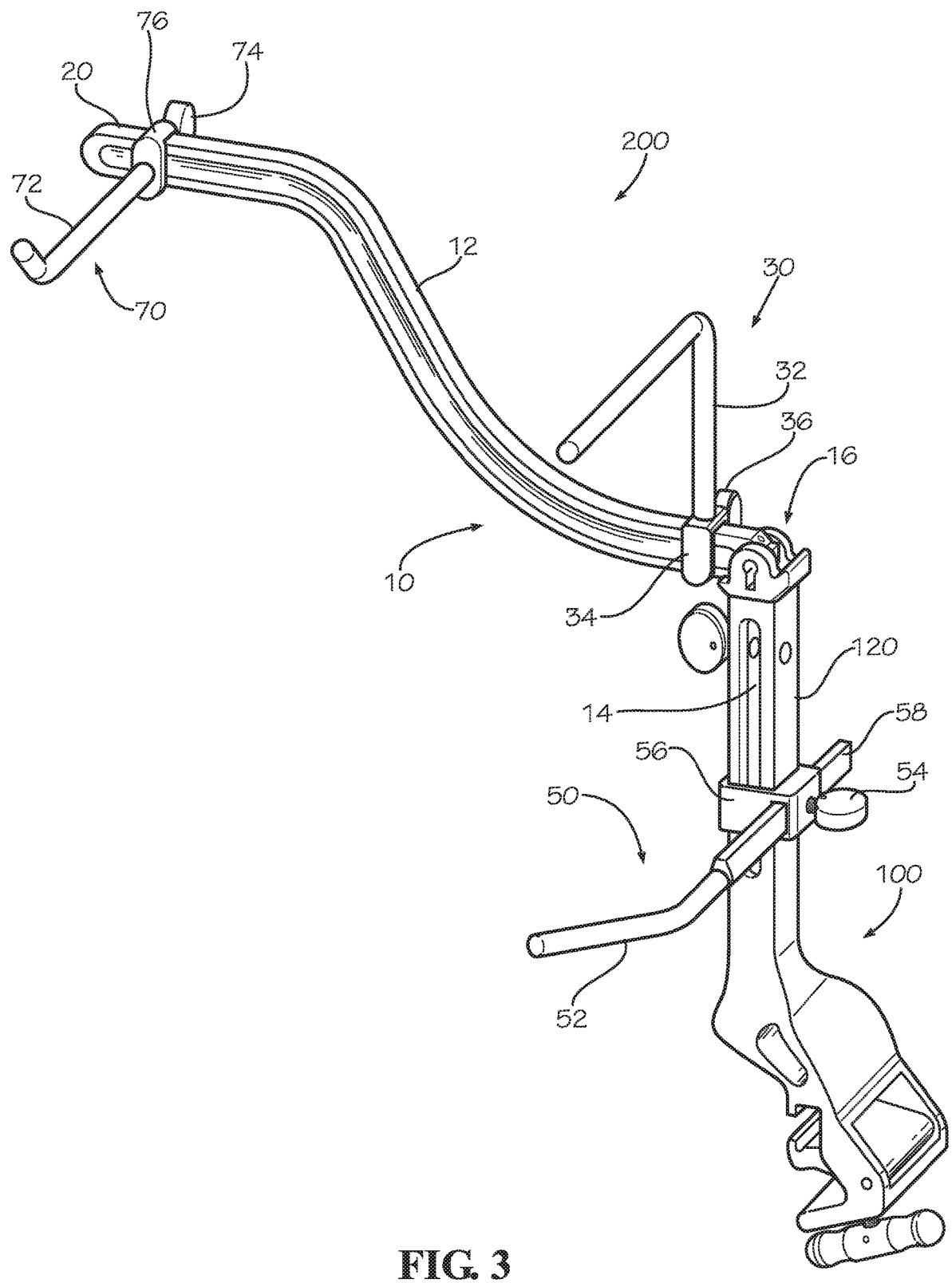
FIG. 3 illustrates a perspective view of an embodiment of an arm positioner device in accordance with the present disclosure.
Figure 4:
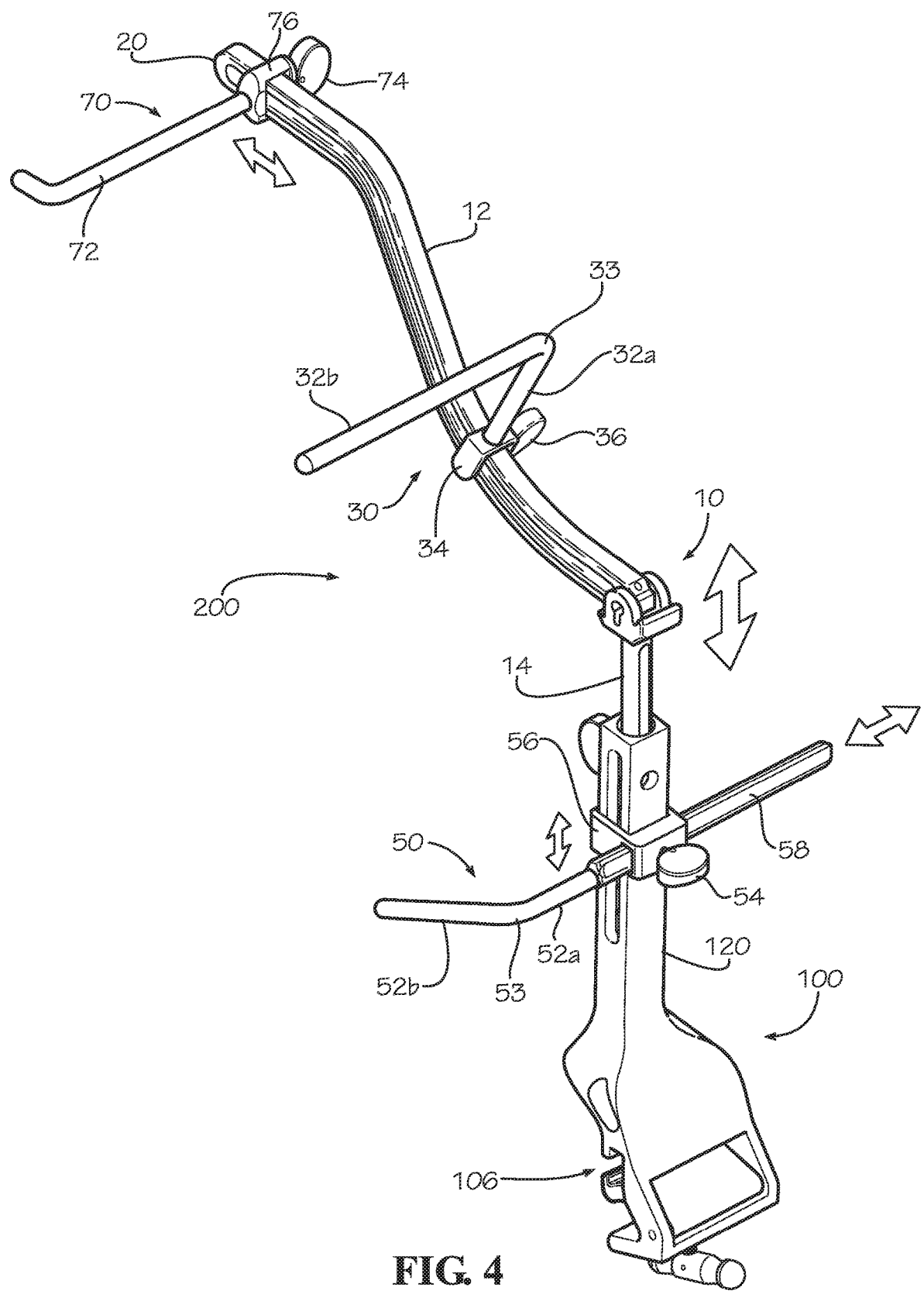
FIG. 4 illustrates a perspective view of an alternative embodiment of an arm positioner device in accordance with the present disclosure.

Base 14 is secured in place on rail clamp 100 using a socket fastener 108 in some embodiments. Socket fastener 108 includes a threaded fastener inserted in a transverse threaded bore in the clamp body 120 on rail clamp 100. Socket fastener 108 may be tightened against a portion of base 14 housed in socket 128 to secure the base 14 in place at a desired vertical position, as seen in FIG. 3 and FIG. 4. Base 14 is longitudinally adjustable relative to rail clamp 100 in some embodiments, as seen in FIG. 4. Socket fastener 108 may be loosened, and base 14 may be slid up or down to accommodate patients of different sizes. When a proper position is reached, socket fastener 108 is re-tightened to hold the base 14 in place. The ability to load and unload base 14 into or away from rail clamp 100 in a longitudinal orientation provides an advantage over other loading configurations in some applications because a longitudinal configuration allows displacement of the base 14 substantially parallel to a patient's humeral region without causing the support arm to interfere with the patient's arm and without having to reposition the rail clamp.

Referring further to FIGS. 1-4, rail clamp 100 also includes a clamp groove 102 in some embodiments. Clamp groove 102 generally includes a recess defined on the clamp body 120 forming a channel for attachment of one or more modular components. Clamp groove 102 includes a blind recess in some configurations forming a slight channel for receiving a corresponding structure. The clamp groove 102 allows a modular attachment to be slid along the length of the groove for positioning of the attachment. Alternatively, clamp groove 102 provides a clearance groove that is open to the socket 128 such that the portion of base 14 extending into socket 128 is visible through the clearance in the clamp groove 102. In such configurations, a user may be able to visually inspect the vertical location of base 14 in socket 128. This allows a user to ensure the base is sufficiently installed a proper depth into socket 128 to provide adequate support. If base 14 does not extend far enough into socket 128, support arm 10 may inadvertently become loosened from the rail clamp 100 and allow undesirable motion during use. By providing a clamp groove 102 having a clearance section, it is possible to visually verify the base 14 is located at a proper position in the socket 128. Accordingly, in some embodiments, base 14 has indicia at a predetermined location such that a user may visually inspect the location of base 14 relative to socket 128.

Clamp body 120 provides a mounting location for one or more modular attachments. As seen in FIGS. 2-4, a humeral support attachment 50 is mounted on rail clamp 100 in some embodiments. More specifically, humeral support attachment 50 includes humeral support mount 56 shaped to be installed on rail clamp 100. Humeral support mount 56 may be slid onto clamp body 120. A humeral mount fastener 54 is positioned on humeral support mount 56 to secure humeral support attachment 50 at a desired location on rail clamp 100. Humeral mount fastener 54 includes a threaded fastener extending through a corresponding threaded hole in humeral support mount 56 in some embodiments. The humeral support mount 56 may be slid up or down along the longitudinal length of clamp body 120 on rail clamp 100 and secured at a desired location using humeral mount fastener 54.

A humeral support bar 52 protrudes from humeral support mount 56 in some embodiments. Humeral support bar 52 extends generally transverse to the longitudinal orientation of rail clamp 100 in some applications. Humeral support bar 52 includes a slide 58 disposed through a humeral mount opening in humeral support mount 56 in some embodiments. Slide 58 is moveable through the humeral mount opening to allow the humeral support bar 52 to be selectively repositioned relative to the rail clamp 100. As such, a user may modify the distance the humeral support bar 52 extends from rail clamp 100. This may be advantageous when configuring the device to support patients of different sizes. Humeral support bar 52 may be positioned to extend laterally from either side of rail clamp 100.

As seen in FIG. 4, in some embodiments, humeral support bar includes a first humeral support bar section 52a and a second humeral support bar section 52b separated at a humeral support bar bend 53. The first and second humeral support bar sections are angled at a generally obtuse angle. In some embodiments, this angle is between about 180 degrees and about 140 degrees. The slight angle between these sections provides improved support of the humeral section of the patient's arm during use.

In some embodiments, humeral mount fastener 54 secures the humeral support bar 52 in place by applying force against the slide region 58 of humeral support bar 52 and also secures the humeral support mount 56 in place relative to the rail clamp 100. Tightening the humeral mount fastener 54 applies force against the slide region 58 on the humeral support bar 52. The applied force presses the other side of the slide region 58 against the surface of the clamp body 120 on the rail clamp 100, thereby securing both the humeral support bar 52 and the humeral support mount 56 in place relative to the rail clamp 100. In some embodiments, the present invention provides a humeral support attachment including a humeral support bar that is moveable in two axes relative to the rail clamp. Specifically, the humeral support bar is vertically moveable along the longitudinal direction of the clamp body and is also moveable transverse to the clamp body in the longitudinal direction of the humeral support bar. This provides an advantage over conventional humeral support devices that may be fixed in place relative to the rail clamp or otherwise limited to adjustment along only one axis.

In additional embodiments, other modular attachments may be affixed to the rail clamp 100.

Referring further to FIGS. 3-4, in further embodiments one or more modular attachments may also be secured to the stabilizer bar 12 on support arm 10. Stabilizer bar 12 includes a longitudinal bar having a proximal bar end 18 located near base 14 and a distal bar end 20 extending away from base 14. One or more modular attachments may be secured to the stabilizer bar 12 between the proximal and distal bar ends. For example, a wrist support attachment 70 is secured to the stabilizer bar 12 on support arm 10 in some embodiments. Wrist support attachment 70 provides a structure for supporting a wrist, forearm or hand region on a patient during use. Wrist support attachment 70 includes a wrist support mount 76 and a wrist support bar 72 protruding from the wrist support mount 76 in a direction away from the stabilizer bar 12. Wrist support mount 76 engages the stabilizer bar 12 and includes a wrist support fastener 74 for securing the wrist support attachment 70 to the stabilizer bar 12 in some embodiments. Wrist support fastener 74 includes a threaded fastener in some embodiments. Wrist support fastener 74 applies a force against the side of the stabilizer bar 12 to secure the wrist support attachment 70 in place. Wrist support attachment 70 may be repositioned along the length of the stabilizer bar 12 by loosening the wrist support fastener 74, repositioning the wrist support mount 76 to a desired location along the length of stabilizer bar 12, and then retightening wrist support fastener 74. The ability to reposition the wrist support attachment 70 relative to the stabilizer bar 12 provides an advantage over other supports that are fixed in place.

As seen in FIG. 4, in some embodiments, wrist support bar 72 includes an angled end to further support a patient's wrist, hand or forearm and to keep the patient's extremity from inadvertently sliding off the end of the wrist support bar 72. Additionally, a mounting groove may be defined in the stabilizer bar 12 along the length of the stabilizer bar 12. One or more structures on the wrist support mount 76 extend at least partially into the mounting groove on the stabilizer bar 12. As such, the mounting groove in the stabilizer bar operates as a track along which the wrist support mount 76, or any other modular attachment, may slide during adjustment of the attachment.

Referring further to FIGS. 3-4, another type of attachment known as a reducer attachment 30 may be positioned on the stabilizer bar 12. Reducer attachment 30 provides structural support for a patient's humeral region, elbow, or forearm during use, and may be use to apply forces to reduce one or more fractures in the arm, wrist or hand. In some applications, a reducer support 32 extends from a reducer mount 34 on the reducer attachment. Reducer support 32 may be located near a patient's elbow joint when a patient is lying in a supine position on an operating table. The reducer support 32 supports an underside portion of a patient's arm and provides a reaction structure against which a physician may apply force during an operation on the patient's arm or elbow for indirect distal humerus fracture reduction or proximal ulna fracture reduction.

Referring further to FIG. 4, reducer attachment 30 includes a generally L-shaped reducer support 32 in some embodiments including a first reducer support section 32a and a second reducer support section 32b oriented at an angle relative to the first reducer support section 32a. These two sections join at a reducer attachment elbow 33 and form a substantially right angle in some embodiments. The second reducer support section 32b extends away from the stabilizer bar 12 and provides support to the user's arm.

The reducer attachment 30 includes a reducer mount 34 that engages the stabilizer bar 12. A reducer fastener 36 on the reducer mount 34 provides a force against the stabilizer bar 12 to secure the reducer attachment 30 in position.

Reducer fastener 36 includes any suitable fastener such as a threaded fastener for applying force against the stabilizer bar 12. A user may adjust the position of the reducer attachment 30 on the stabilizer bar 12 by loosening the reducer fastener 36, repositioning the reducer attachment at a desired location along the length of the stabilizer bar 12, and then retightening the reducer fastener 36. In some embodiments, the reducer fastener 36 engages a mounting groove on the stabilizer bar 12, where the mounting groove operates as a track along which the reducer mount 34 may be slid for positioning the reducer attachment 30.

The arm positioner device 200 of the present disclosure may be configured in numerous ways, depending on which attachments are mounted on the device. For example, the reducer attachment 30 may be used on the arm positioner device 200 as the only modular attachment. For example, in some embodiments, the arm positioner device 200 includes only the rail clamp 100, the support arm 10 and the reducer attachment 30. In other embodiments, arm positioner device 200 includes only the rail clamp 100, and humeral support attachment 50. In further embodiments, the arm positioner device 200 includes only the rail clamp 100, support arm 10, humeral support attachment 50, and wrist support attachment 70. In additional embodiments, the arm positioner device 200 includes only the rail clamp 100, support arm 10, and wrist support attachment 70. In further embodiments, the arm positioner device 200 includes only the rail clamp 100, support arm 10, wrist support attachment 70, and humeral support attachment 50. In yet other embodiments, the arm positioner device 200 includes the rail clamp 100, support arm 10, wrist support attachment 70, humeral support attachment 50 and reducer attachment 30.

Figure 6:
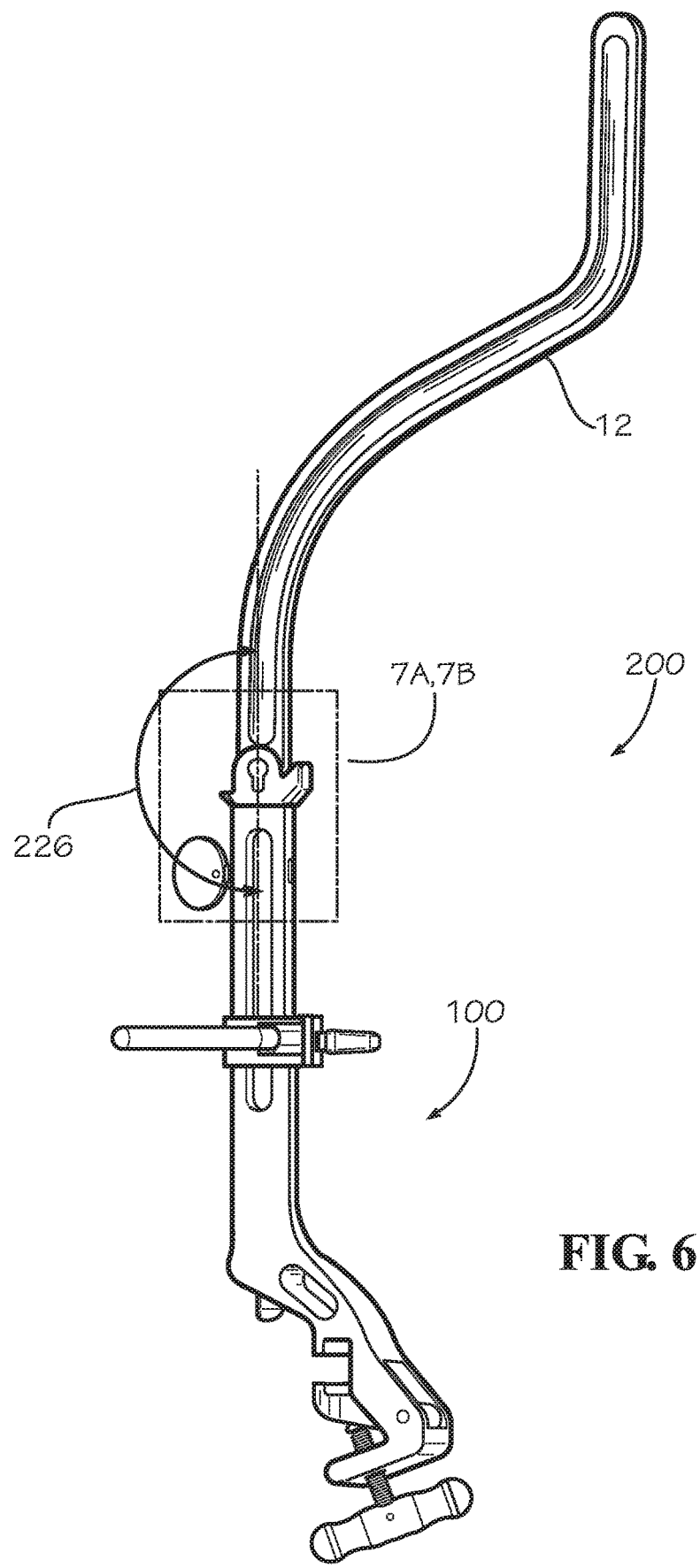
FIG. 6 illustrates a side elevation view of an alternative embodiment of an arm positioner device with a support arm in a second angular position relative to the rail clamp in accordance with the present disclosure.

Another attachment for the arm positioner system includes a wrist tower attachment that may be used to orient a patient's arm, wrist and/or hand in a suspended supine position for distraction of the arm, wrist and/or hand for various operations. The wrist tower attachment is a modular device that may be installed on the support arm 10, or supine positioner. To mount a wrist tower attachment on the device, the stabilizer bar 12 of the supine positioner is generally repositioned such that the distal end 20 of the stabilizer bar 12 extends in an upright orientation as shown in FIG. 6. In some embodiments, the stabilizer bar 12 may be adjusted relative to the base 14 on the supine positioner such that the distal bar end 20 is oriented substantially vertically. Such a configuration allows the modular wrist tower attachment to be installed on the distal bar end 20.

Figure 5:
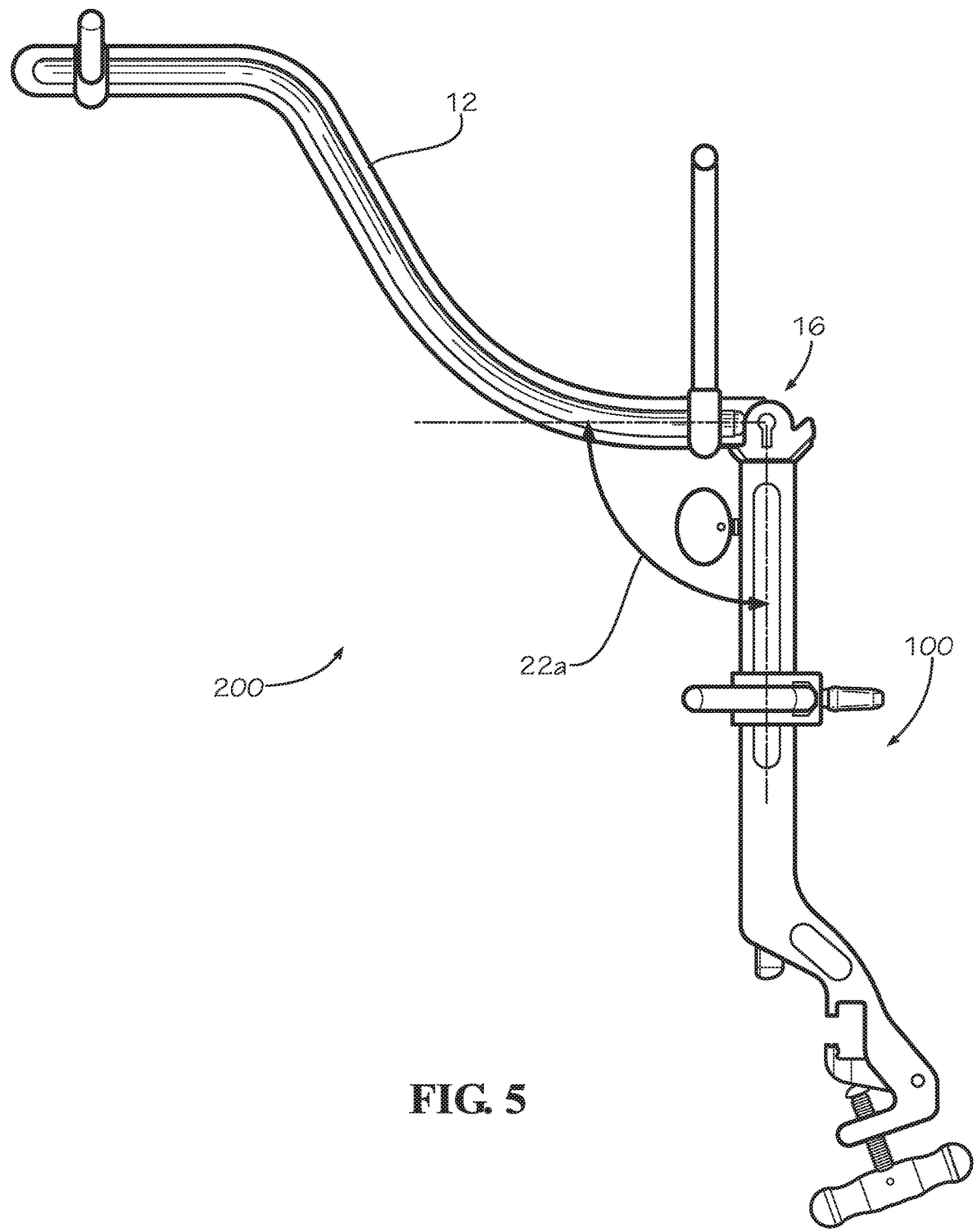
FIG. 5 illustrates a side elevation view of an embodiment of an arm positioner device with a support arm in a first angular position relative to the rail clamp in accordance with the present disclosure.

Referring further to FIGS. 5-7B, in some embodiments the stabilizer bar 12 is angularly moveable relative to the base 14 when the base is secured in the rail clamp 12. As such, stabilizer bar 12 is also angularly moveable relative to rail clamp 100 when base 14 is installed in the rail clamp. As seen in FIG. 5, stabilizer bar 12 may be oriented relative to rail clamp 100 at a first angle 22a. The first angle may be approximately ninety degrees in some embodiments. A first angle stop 78, shown in FIG. 7A, on support arm 10 provides an angular stop for stabilizer bar 12. Stabilizer bar 12 is attached to base 14 at a base hinge 16 in some embodiments. Stabilizer bar 12 may be angularly rotated back as shown in FIG. 6 to a second angle greater than ninety degrees.

Figure 7A:
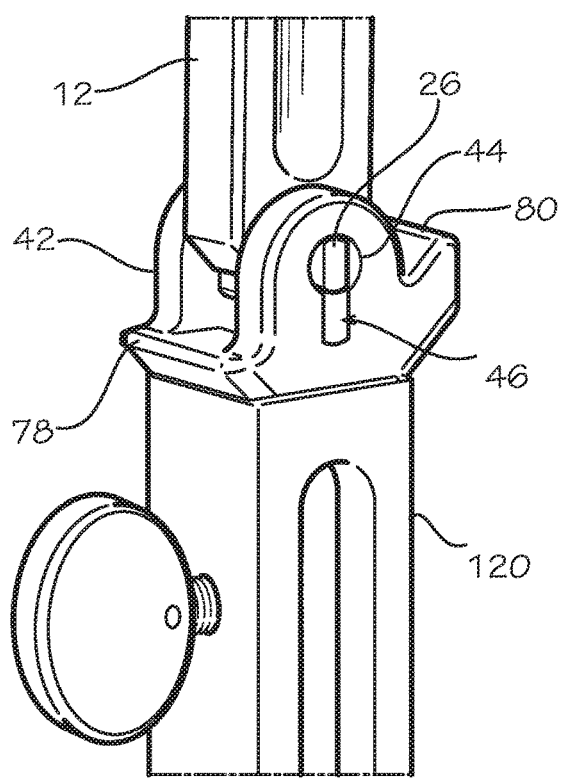
FIG. 7A illustrates a detail perspective view of Section 7A of the embodiment of an arm positioner device from FIG. 6.
Figure 7B:
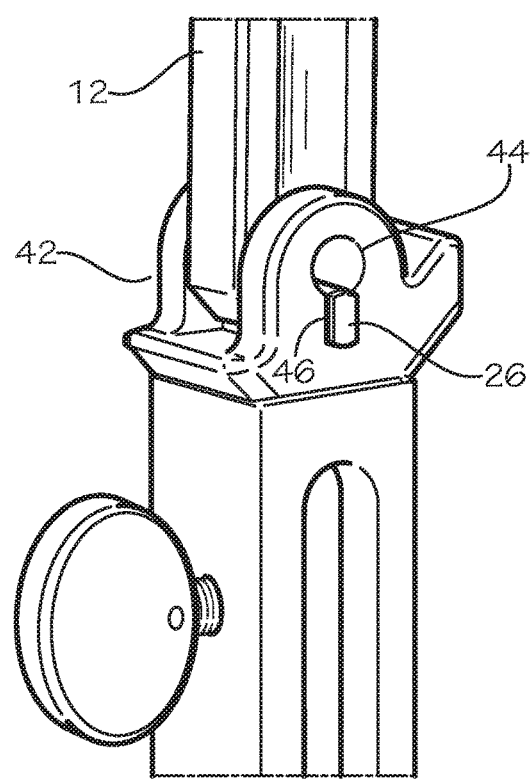
FIG. 7B illustrates a detail perspective view of Section 7B of the embodiment of an arm positioner device from FIG. 6.

In some embodiments, support arm 10 includes an angular lock to secure stabilizer bar 12 at a desired angle. For example, as seen in FIGS. 7A and 7B, a base head 42 is positioned on base 14 in some embodiments. Base head 42 includes a pivot opening 44. A locking pin 26 attached to stabilizer bar 12 extends transversely through and is rotatable in pivot opening 44. A locking slot 46 adjoins and is open to pivot opening 44. Locking pin 26 includes a substantially flat dimension shaped to be received in locking slot 46. Locking pin 26 may slide into locking slot 46, as seen in FIG. 7B, when stabilizer arm 12 is positioned at a corresponding angular position. In some applications, the angular lock is configured to selectively lock stabilizer bar 12 in a substantially vertical configuration, as seen in FIG. 6. When a user desires to unlock the angular lock, the stabilizer bar 12 may simply be lifted up to disengage locking pin 26 from locking slot 46, thereby allowing free rotation of locking pin 26 in pivot opening 44 and corresponding rotation of stabilizer bar 12 relative to base 14.

In some applications, it is desirable to provide a back angular stop on support arm 10 such that stabilizer bar 12 does not rotate too far away from the patient during use. As such, a second angular stop 80, seen in FIG. 7A, is positioned on base head 42 in some embodiments. Second angular stop allows support arm 10 to be rotated away from a patient when not in use.

Figure 8:
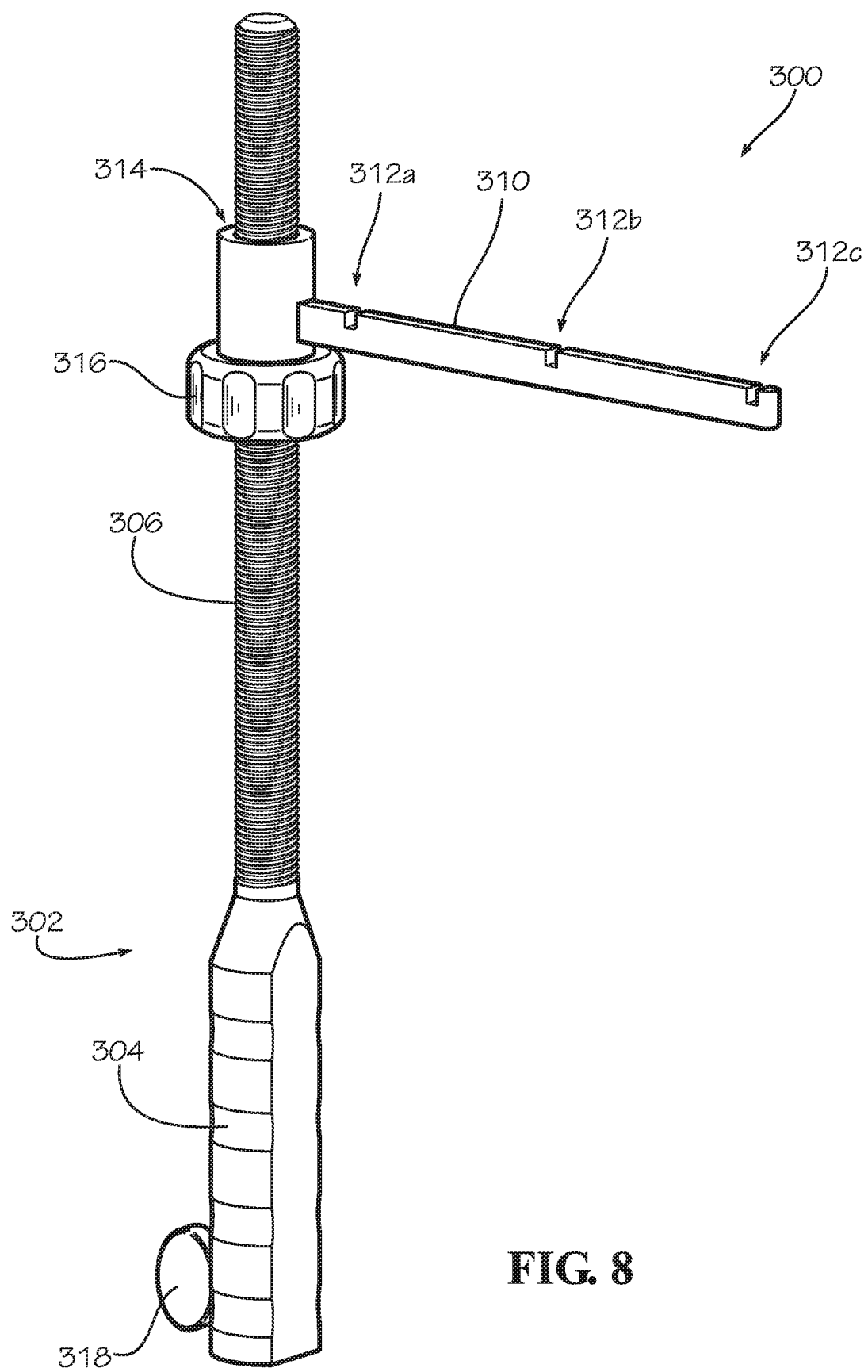
FIG. 8 illustrates a perspective view of an embodiment of a wrist tower attachment apparatus for use on an arm positioner device.

Additionally, in some applications, stabilizer bar 12 may be rotated away from the patient to provide a different type of support. For example, a modular wrist tower attachment 300 as shown in FIG. 8 may be attached to stabilizer bar 12 when tilted back in the upright position. Modular wrist tower attachment 300 may be used to provide support to a patient's arm, wrist and/or hand during various types of medical procedures.

An embodiment of a wrist tower attachment 300 as shown in FIG. 8 includes a wrist tower base 304 and a wrist tower post 306 extending upwardly from the wrist tower base 304. Wrist tower post 306 includes a threaded rod in some embodiments. In other embodiments, wrist tower post 306 may include any suitable threaded or non-threaded structure protruding upwardly from the wrist tower base 304.

Figure 9:
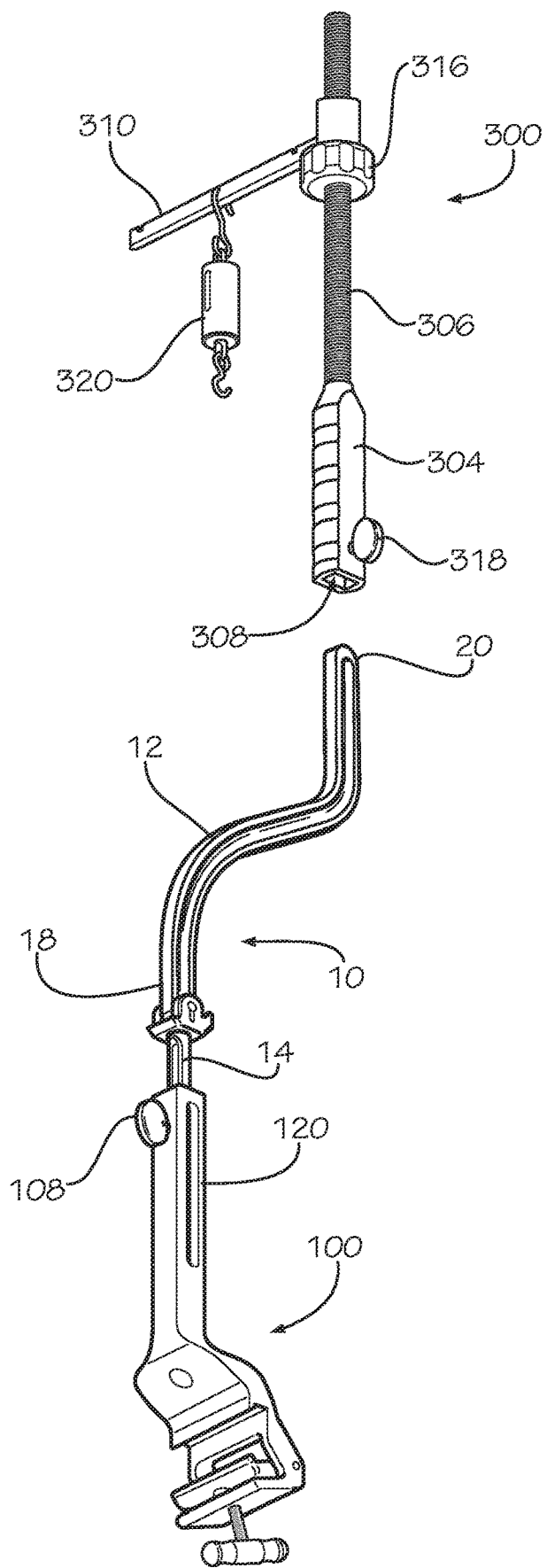
FIG. 9 illustrates a partially-exploded perspective view of an embodiment of an arm positioner device including a wrist tower attachment apparatus.

Wrist tower base 304 includes an open socket 308, seen in FIG. 9. The open socket 308 provides a space to receive the distal bar end 20 on stabilizer bar 12. When stabilizer bar 12 is in the upright position, wrist tower attachment 300 may be installed onto the stabilizer bar 12 by axially sliding the distal bar end 20 of stabilizer bar 12 into the open socket 308 on wrist tower base 304. A wrist tower fastener 318 on wrist tower base 304 may then be tightened to secure the wrist tower attachment 300 on the distal bar end 20 of the stabilizer bar 12 on support arm 10.

In some embodiments, the open socket 308 includes a blind socket with a depth dimensioned such that the distal bar end 20 of stabilizer bar 12 extends to the upper limit of the interior of the socket. During use, the position of wrist tower attachment 300 relative to stabilizer bar 12 may be adjusted by loosening wrist tower attachment fastener 318 and axially repositioning wrist tower base 304 along the length of the distal bar end 20.

Wrist tower attachment 300 also includes a wrist traction bar 310, or traction hanger, extending radially from wrist tower post 306. Wrist traction bar 310 forms a rigid structure for hanging one or more items such as tension gauge 320 or one or more straps or finger traps for applying traction to a patient's fingers, hand, wrist or arm. Wrist traction bar 310 includes one or more slot locations 312a, 312b, 312c to provide variability in the direction and location of applied distraction force.

Figure 10:
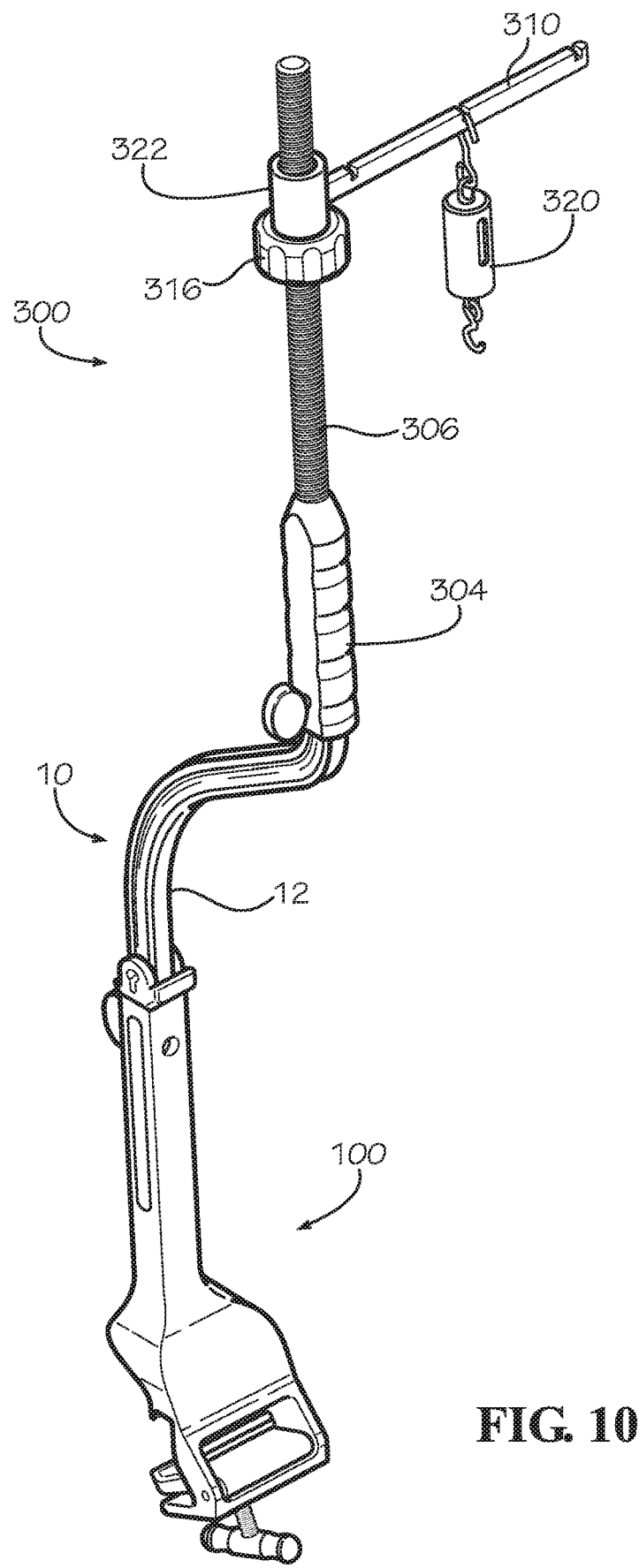
FIG. 10 illustrates a perspective view of an embodiment of an arm positioner device including a wrist tower attachment apparatus.

In some embodiments, as seen in FIGS. 8-10, a traction bar fastener 316 is disposed on wrist tower post 302. Traction bar fastener 316 provides an adjustable vertical stop for wrist traction bar 310 so that the vertical position of wrist traction bar 310 may be precisely adjusted to accommodate patients of different sizes or to apply variable forces on the arm, wrist and/or hand. Traction bar fastener 316 includes a threaded nut, or threaded washer, disposed on the threaded region of wrist tower post 302. Traction bar fastener 316 may be threadedly adjusted to different vertical positions along the length of wrist tower post 302. Traction bar fastener 316 includes a knurled or textured outer perimeter to allow a physician to obtain a grip on traction bar fastener 316 to make manual adjustments.

Wrist traction bar 310 also includes a traction bar collar 322 disposed on wrist tower post 306. Traction bar collar 322 includes a collar bore 314 through which wrist tower post 306 extends. In some embodiments, collar bore 314 includes a smooth bore allowing traction bar collar 322 and traction bar 310 to spin freely angularly around wrist tower post 306. As such, the traction bar fastener 316 provides a vertical stop for traction bar collar 322 and traction bar 310.

In alternative embodiments, collar bore 314 on traction bar collar 322 is threaded, and collar bore 314 threadedly engages corresponding threads on wrist tower post 306. Traction bar fastener 316 may be tightened against traction bar collar 322 in such embodiments to rigidly lock traction bar 310 and traction bar collar 322 at a desired height and angular orientation.

Figure 11:
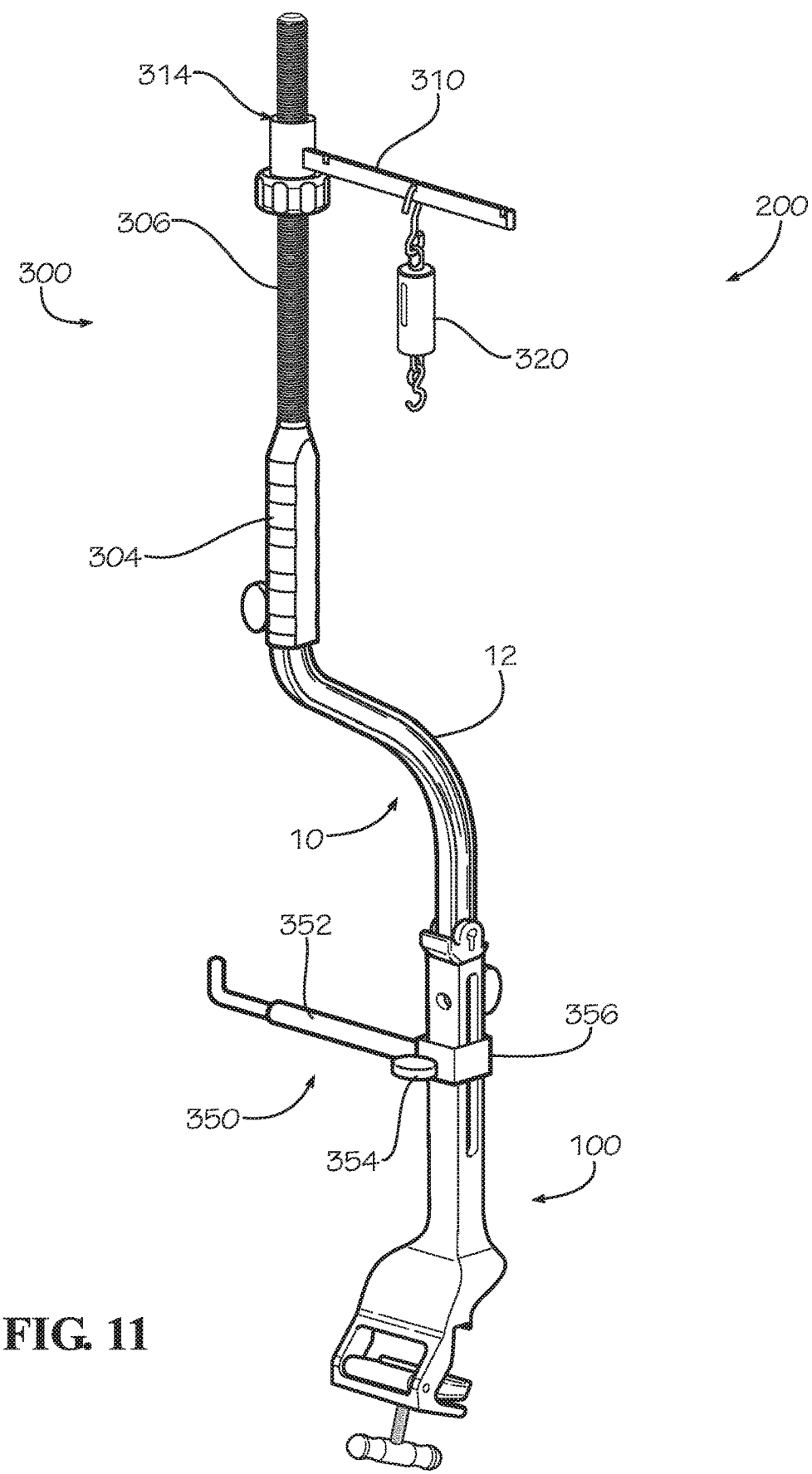
FIG. 11 illustrates a perspective view of an embodiment of an arm positioner device including a wrist tower attachment apparatus.

Referring to FIG. 11, in some embodiments, arm stabilizer apparatus 200 includes four main components, including a rail clamp 100 and a support arm 10 installed on the rail clamp 100. The support arm 10 includes a base and a stabilizer bar 12 positioned in an upright orientation. A wrist tower attachment 300 is disposed on the distal end of the stabilizer bar 12. The wrist tower attachment 300 includes a wrist tower base 304 and a wrist tower post 306 protruding upwardly from the wrist tower base 304. A wrist tower traction bar 310 is disposed on the wrist tower post 306.

Figure 13:
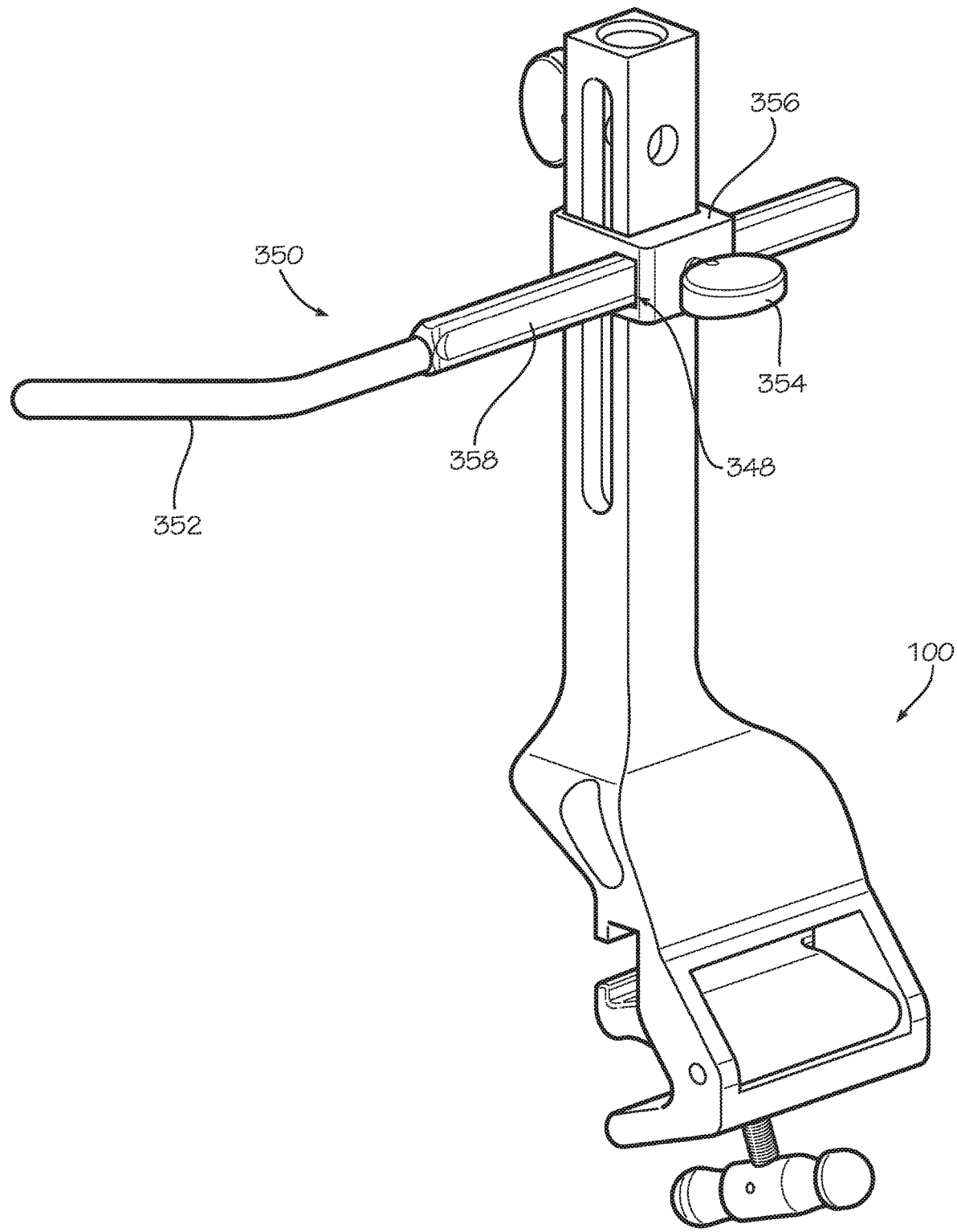
FIG. 13 illustrates a perspective view of an embodiment of an arm positioner device including a wrist tower attachment apparatus.

Additionally, as seen in FIG. 11 and FIG. 13, in some embodiments a separate modular attachment forming a counter-traction bar 350 is also included on rail clamp 100. Counter-traction bar 350 extends from a counter-traction bar mount 356 engaging rail clamp 100. Counter-traction bar mount 356 is secured to rail clamp 100 using a counter-traction bar fastener 354 in some embodiments. Counter-traction bar 350 may be repositioned along height of rail clamp 100 to accommodate patients of different sizes. Although counter-traction bar 350 is illustrated extending from the left side of rail clamp 100 in FIG. 11, counter-traction bar 350 may be positioned to extend from either side of rail clamp 100 during use. When a patient's arm and/or hand is suspended from wrist traction bar 310, a portion of the patient's arm or torso may be placed under the counter-traction bar 350 such that the counter-traction bar applies an opposing, counter-traction force on the patient's body. In some embodiments, humeral support 50 may be interchangeably used as counter-traction bar 350 in a suspended supine position. The counter-traction bar 350 attachment may be repositioned on the device to perform different functions in various embodiments.

Figure 12:
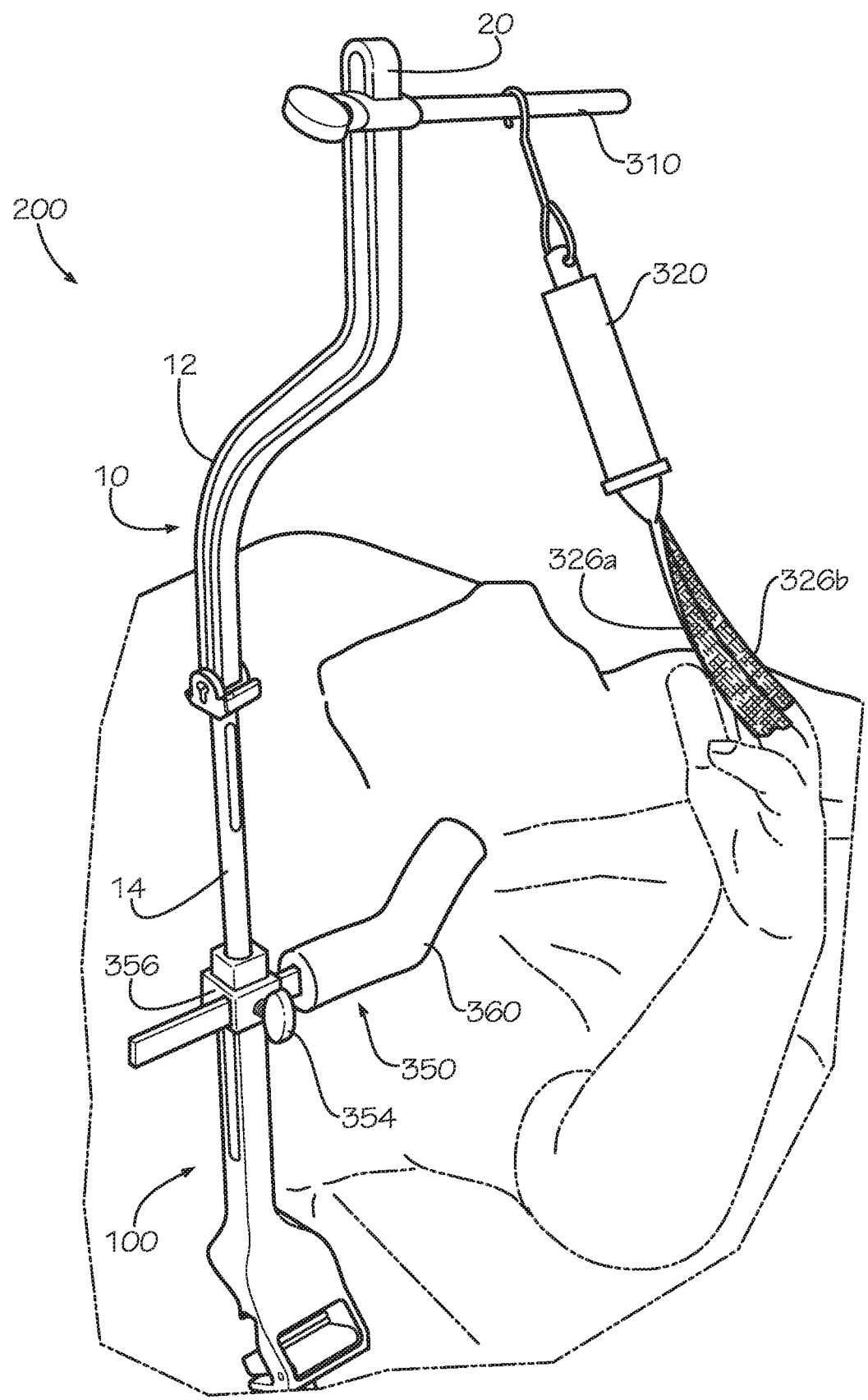
FIG. 12 illustrates a perspective view of an embodiment of an arm positioner device including a wrist tower attachment apparatus.

As seen in FIG. 12, an alternative embodiment of an arm positioner device 200 includes a rail clamp 100, a support arm 10 including a base 14 and a stabilizer bar 12 connected at a pivoting joint. A wrist tower traction bar 310 is disposed on the distal bar end 20 on stabilizer bar 12. A tension gauge 320 is disposed on the traction hanger 310, and one or more anterior finger traps 326a, 326b are secured to the tension gauge 320. During use, a patient's arm may be maintained in suspended supine orientation when the anterior finger traps engage the patient's fingers. In such embodiments, a counter-traction bar 350 may be secured to the rail clamp 100 or support arm 10 and extend toward the patient. The counter-traction bar 350 provides a counter-traction force against the patient's arm and allows the desired applied traction force to be applied, as measured by the tension gauge 320.

As seen in FIG. 12, in some embodiments, counter-traction bar 350 includes a rigid member extending toward the patient a sufficient distance to engage a portion of the patient's body to apply a counter-traction force. Counter traction bar 350 is axially moveable along the counter-traction mount 356 in some embodiments. Counter-traction bar mount 356 includes a passage allowing axial travel of counter-traction bar 350 in some embodiments. A counter-traction bar fastener 354 may be tightened against counter-traction bar 350 to secure counter-traction bar 350 at a desired axial position relative to the rail clamp. Additionally, counter-traction bar fastener 354 in some embodiments is also operable to engage rail camp 100 to secure the counter-traction bar mount 356 at a desired location along the height of rail clamp 100. A counter-traction bar pad 360 is disposed on counter-traction bar 350 in some embodiments.

In some applications, the configuration shown in FIG. 12 requires the base 14 to be vertically raised out of the rail clamp to such a height that the stabilizer bar 12 becomes unstable. In such applications, it is desirable to affix the wrist tower apparatus 300 onto the distal bar end 20 of stabilizer bar 12.

Thus, although there have been described particular embodiments of the present invention of a new and useful Wrist Tower Device and Methods, it is not intended that such references be construed as limitations upon the scope of this invention except as set forth in the following claims.

What is claimed is:

1. A wrist tower apparatus for attachment to an arm positioning device for positioning a patient's arm in a suspended supine orientation, the apparatus comprising:
   a wrist tower attachment including a vertical wrist tower base and a vertical wrist tower post protruding upwardly from the vertical wrist tower base, the vertical wrist tower post including an upper end and a lower end;
   a vertical axial socket, wherein the vertical axial socket
      is defined at the lower end of the vertical wrist tower post inside the vertical wrist tower base
      has a blind end defined in the vertical wrist tower base, the blind end being disposed toward the lower end of the vertical wrist tower post,
      is positioned in the vertical wrist tower base to receive the arm positioning device, and
      is axially aligned with the vertical wrist tower post;
   a traction bar including a traction bar collar disposed on the vertical wrist tower post, the traction bar extending radially from the vertical wrist tower post;
   a traction bar passage defined in the traction bar collar on the traction bar, the traction bar passage shaped to receive the vertical wrist tower post through the traction bar passage; and
   an axial stop disposed on the vertical wrist tower post between the vertical wrist tower base and the traction bar, wherein the axial stop is moveable between multiple positions along the length of the vertical wrist tower post, and wherein the axial stop engages and supports the traction bar collar.

2. The apparatus of claim 1, further comprising a tension gauge disposed on the traction bar.

3. The apparatus of claim 2, wherein the vertical wrist tower post comprises a threaded rod.

4. The apparatus of claim 3, wherein the axial stop comprises a threaded nut threadedly engaging the threaded rod of the vertical wrist tower post.

5. The apparatus of claim 4, wherein the traction bar passage is threaded.

6. The apparatus of claim 4, wherein the traction bar passage is not threaded.

7. The apparatus of claim 1, wherein the traction bar is freely angularly moveable around the vertical wrist tower post.

* * * * *